(12) United States Patent
Easterling et al.

(10) Patent No.: US 7,851,431 B2
(45) Date of Patent: Dec. 14, 2010

(54) TREATMENT OF ACTINIC KERATOSES WITH CALCIUM CHANNEL BLOCKERS

(75) Inventors: W. Jerry Easterling, San Antonio, TX (US); Michael J. Bordovsky, San Antonio, TX (US)

(73) Assignee: Prescription Dispensing Laboratories, San Antonio, TX (US)

( * ) Notice: Subject to any disclaimer, the term of this patent is extended or adjusted under 35 U.S.C. 154(b) by 674 days.

(21) Appl. No.: 11/459,562

(22) Filed: Jul. 24, 2006

(65) Prior Publication Data

US 2007/0027194 A1 Feb. 1, 2007

Related U.S. Application Data

(60) Provisional application No. 60/703,042, filed on Jul. 27, 2005.

(51) Int. Cl.
  *A01N 61/00* (2006.01)
  *A01N 43/00* (2006.01)
  *A01N 33/02* (2006.01)
  *A01N 43/40* (2006.01)

(52) U.S. Cl. .................. 514/1; 514/211.09; 514/649; 514/277

(58) Field of Classification Search .................. None
See application file for complete search history.

(56) References Cited

U.S. PATENT DOCUMENTS

| | | | |
|---|---|---|---|
| 6,031,005 A | 2/2000 | Easterling | 514/654 |
| 6,353,028 B2 | 3/2002 | Easterling | 514/654 |
| 6,525,100 B1 | 2/2003 | Easterling et al. | 514/654 |
| 2002/0022664 A1* | 2/2002 | Easterling | 514/654 |
| 2004/0170675 A1 | 9/2004 | Easterling | 424/449 |
| 2004/0171684 A1 | 9/2004 | Easterling | 514/519 |
| 2004/0248099 A1* | 12/2004 | Goppelt et al. | 435/6 |

FOREIGN PATENT DOCUMENTS

WO  WO 02/053171  *  7/2002

OTHER PUBLICATIONS

Mauro et al., Keratinocyte K+ Channels Mediate Ca2+-Induced Differentiation, 1997, The Society for Investigative Dermatology, Inc., 108 (6), 864-870.*
"Topical diclofenac: new preparation. Moderate efficacy in actinic keratosis," *Prescrire Int.*, 13:138-139, 2004.
Fitscha et al., "The Diminished Extracellular Matrix Production Induced by Isradipine, a Calcium Channel Blocker, is Completely Abolished by Cyclooxygenase Inhibition," *Prost. Leukot. Essent. Fatty Acids*, 45:289-291, 1992.
Jeffes and Tang, "Actinic keratosis. Current treatment options," *Am. J. Clin. Dermatol.*, 1:167-179, 2000.
Jorizzo et al., "Treatment Options in the Management of Actinic Keratosis," *Cutis*, 6(Suppl.):9-7, 2004.
Lober and Fenske, "Optimum treatment strategies for actinic keratosis (intraepidermal squamous cell carcinoma)," *Am. J. Clin. Dermatol.*, 5:395-401, 2004.
Rodler et al., "Ca(2+)-channel blockers modulate the expression of interleukin-6 and interleukin-8 genes in human vascular smooth muscle cells," *J. Mol. Cell Cardiol.*, 27:2295-2302, 1995.
Roth et al., "Ca2+ channel blockers modulate metabolism of collagens within the extracellular matrix," *Proc. Natl. Acad Sci. USA*, 93: 5478-5482, 1996.
Stetler-Stevenson, "Dynamics of Matrix Turnover Durin Pathologic Remodeling of the Extracellular Matrix," *Amer. J. Pathol.*, 148:1345-1350, 1996.

* cited by examiner

*Primary Examiner*—Frederick Krass
*Assistant Examiner*—Gigi Huang
(74) *Attorney, Agent, or Firm*—Fulbright & Jaworski L.L.P.

(57) ABSTRACT

The present invention relates to methods and compositions for the treatment and/or prevention of actinic keratoses comprising a calcium channel blocking compound.

15 Claims, No Drawings

TREATMENT OF ACTINIC KERATOSES WITH CALCIUM CHANNEL BLOCKERS

BACKGROUND OF THE INVENTION

This application claims the benefit of priority to U.S. Provisional Patent Application Ser. No. 60/703,042, filed Jul. 27, 2005, which has the same title and inventors as the present application, and is hereby incorporated herein by reference in its entirety.

A. Field of the Invention

The present invention relates generally to methods and compositions for the treatment of actinic keratoses. In particular, the present invention is directed towards compositions comprising calcium channel blocking compounds and related methods for their use in treating and/or preventing actinic keratoses.

B. Background of the Invention

Actinic keratoses (AK), also known as solar keratoses, have been considered to be premalignant skin tumors, but are now increasingly viewed as de facto intraepidermal squamal cell carcinomas (Heaphy and Ackerman, 2000; Ackerman, 2001; Lober and Fenske, 2004). Early AK lesions present as patches with the texture of sandpaper or scabs, with the lesions becoming more discrete as they progress due to hyperkeratosis. The lesions also may become erythematous. AK occur predominantly on sun-exposed areas of fair skinned people, and it has been estimated that 60% of predisposed persons older than 40 years of age have at least one actinic keratosis (Frost and Green, 1994; Salasche, 2000). Patients with AK have an increased incidence of developing new AK, making AK a potentially lifelong condition (Frost and Green, 1994).

Surgical treatments such as cryotherapy, excision and laser resurfacing, while effective against discrete lesions, may not address subclinical lesions, and are painful and associated with risks of scarring, infection and pigmentary changes (Jorizzo et al., 2004; Lober and Fenske, 2004). Many AK patients have multiple lesions, not all of which are discrete and obvious. Suggested treatments for such patients include therapeutic options that treat the entire affected area of skin such as topical treatments and photodynamic therapy. Topical treatment, such as 5-fluouracil, imiquimod, and dicolfenac, however, are less effective that surgical options against discrete lesions and have been associated with irritation, allergic reactions, and problems with patient compliance (Jeffes and Tang, 2000; Topical Diclofenac, 2004; Lober and Fenske, 2004). Photodynamic therapy with aminolevulinic acid is approved in the USA for the treatment of AK. Disadvantages of this therapeutic modality include burning, stinging, cost, and an inconvenient treatment schedule wherein the patient must return to the physician within hours of application of the aminolevulinic acid (Lober and Fenske, 2004).

There is a need for products and methods for the effective treatment of AK, preferably that are convenient to use and obviate such side effects as pain, scarring, and irritation.

SUMMARY OF THE INVENTION

The present invention overcomes the deficiencies in the art by providing compositions and methods that can be used to treat AK.

One aspect of the present invention is a method for the treatment and/or the prevention of AK on an area of skin of a subject in need of such treatment, comprising contacting said skin with an effective amount of one or more calcium channel blocker or other agent effective to treat AK, such as a calmodulin blocking agent. In various embodiments, the calcium channel blocker is one or more of a diphenylalkylamine calcium channel blocker, which may be verapamil; a dihydropyridine calcium channel blocker, which may be amlodipine, barnidipine, benidipine cilnidipine efonidipine felodipine, isradipine, nacidipine nercanidipine manidipine, nicardipine, nifedipine, nilvadipine, nimodipine, nisoldipine, or nitrendipine; or a benzothiazepine calcium channel blocker, which may be diltiazem. Weak calcium channel blockers such as magnesium sulfate may also be employed, as well as calmodulin blocking agents such as trifluoperazine. In some preferred embodiments, the agent is verapamil.

In some embodiments, the area of skin in need of treatment is contacted topically with a formulation comprising the agent effective to treat AK. In some embodiments, the agent is present in the formulation in range of about 1% to about 30% by weight. More specific embodiments may comprise about 5% to about 20% agent by weight, and some particular embodiments comprise 10% to about 15% agent by weight. In particular, verapamil may be used at all of these concentrations in some embodiments.

In some embodiments, the formulation comprises one or more additional components. By way of example, these include agents that facilitates spreading or application of the composition on a surface, semi-solid and gel-like vehicles, thickening agents, water, preservatives, emulsifiers, antioxidants, sunscreens, solvents, absorbents, fragrances, essential oils, skin sensates, anti-caking agents, antifoaming agents, antimicrobial agents, binders, biological additives, buffering agents, bulking agents, chemical additives, denaturants, polymer beads, film formers or materials, opacifying agents, pH adjusters, propellants, reducing agents, and sequestrants.

For example, the additional component may be an agent that facilitates the spreading or application of a composition on a surface. Non-limiting examples of such agents include isopropyl myristate and lecithin soya granular. In a particular embodiment, the formulation includes isopropyl myristate and lecithin soya granular in approximately equal amounts by weight. For example, the amount of agent that facilitates the spreading or application may be in the range of about 5% to about 50% by weight, about 10% to about 40% by weight, about 20% to about 35% by weight, or in a range of about 25% to about 30% by weight.

In some embodiments, the formulation includes a surfactant. Many surfactants are know to those of skill in the art, and a non-limiting example is pluronic F127. For example, in some embodiments, the surfactant in the formulation may be in the range of about 1% to about 30% by weight, about 5% to about 20% by weight, or about 8% to about 14% by weight. In some embodiments, the formulation comprises a drug solubilizing agent, such as ethoxydiglycol. For example, the drug solubilizing agent may be present in the range of about 1% to about 40% by weight, about 10% to about 25% by weight, or about 14% to about 20% by weight. In some embodiments, the formulation comprises an antioxidant such as BHT (butylatedhydroxytoluene). For example, the antioxidant may be present at about 0.1% by weight. Suitable antimicrobial agents, such as methyl and propyl parabens, may be employed as well as other antimicrobial agents at levels common in the art.

Another aspect of the present invention is an article of manufacture comprising packaging materials, and, contained within the packaging material, at least one calcium channel blocker or other agent that can treat AK ad described above, wherein the packaging material comprises a label that indicates that the at least one calcium channel blocker or other agent can be used to treat actinic keratoses on a patient's skin.

In particular embodiments, the calcium channel blocker is verapamil, preferably provided at a concentration described elsewhere in this specification. In some embodiments, the calcium channel blocker or other agent is provided in a topical formulation. The formulation may include at least one or more additional component, such as any of the classes or specific agents set forth elsewhere in this specification.

The terms "inhibiting," "reducing" or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

I. Calcium Channel Blockers

In typical embodiments of the present invention, the primary active ingredient is verapamil hydrochloride, USP, a diphenylalkylamine. However, in other embodiments of the present invention, other calcium channel blockers are useful in the treatment of AK when administered in a similar fashion. In further embodiments, combinations of channel blocker agents are used. Other calcium channel blockers encompassed by present invention include, but are not limited to, benzothiazepines (diltiazem, for example), dihydropyridines (amlodipine, bamidipine, benidipine cilnidipine efonidipine felodipine, isradipine, nacidipine nercanidipine manidipine., nicardipine, nifedipine, nilvadipine, nimodipine, nisoldipine, nitrendipine,), and the fast sodium inward channel inhibitor bepridil. Diltiazem in particular, may suitably be substituted for verapamil, particularly for patients with a demonstrated skin sensitivity to verapamil. Weak calcium channel blockers such as magnesium sulfate may also be employed, as well as calmodulin blocking agents such as trifluoperazine.

Appropriate dosages when substituting one particular calcium antagonist for another (verapamil for diltiazem, for example) will be made in same manner as is known in the art, i.e., as if such agents were being interchanged for their existing, more conventional uses. Likewise, combining multiple calcium antagonists will result in similar dosage considerations, as will be apparent to persons skilled in the art.

Calcium channel blockers, and verapamil in particular, affect the extracellular matrix by inhibiting the expression of collagen as well as by increasing the proteolytic activity of collagenase, thereby enhancing matrix remodeling by human fibroblasts in bum scars (Fitscha et al., 1992) and vascular smooth muscle cells (Roth et al., 1996; Steler-Stevenson et al., 1996). In addition, verapamil and other calcium channel blockers affect cytokine expression associated with the early phase of wound healing and inflammation, including platelet-derived growth factor BB, interleukin-6 and interleukin-8 (Roth et al., 1996; Rodler et al., 1995). While not being bound by any particular theory, the inventors believe that the effect on the appearance of skin by topical application of calcium channel blockers is in part due to the remodeling of the dermal tissue and such remodeling may also impart benefits to the epidermal tissue. Additionally, calcium channel blockers may enhance the innate and adaptive immune response which may vary depending on many intrinsic and extrinsic factors such as the number of lesions and the extent of tissue damage.

II. Formulations

In typical embodiments, the method of administration is topical application. Disclosed herein are formulations suitable for use in the methods of the present invention; however, the method is not limited to exemplified formulations and encompasses in general suitable vehicles and methods for topical application.

The present invention encompasses all suitable topical formulations as are generally known in the art. As will be evident to one of skill in the art, various formulations, while varying in non-therapeutic attributes, will be suitable and equivalent in the ability to achieve the therapeutic advantages of the present invention. Thus, topical compositions may include carrier components such as are known in the art. Such carriers can include one or more compatible liquid or solid filler diluents or vehicles that are suitable for application to skin. In addition, a variety of components such as are conventionally used in a topical formulation, provided that they do not unacceptably alter the benefits of the invention. These components of topical formulations should be suitable for application to mammalian skin, and more particularly, human skin. Thus, when incorporated into the compositions they are suitable for use in contact with human skin without undue toxicity, incompatibility, instability, allergic response, and the like, within the scope of sound medical or formulator's judgment. The CTFA Cosmetic Ingredient Handbook, Second Edition (1992) describes a wide variety of nonlimiting cosmetic and pharmaceutical ingredients commonly used in the skin care industry, which are suitable for use in the compositions of the present invention. Examples of these ingredient classes include: surfactants, absorbents, aesthetic components such as fragrances, essential oils, skin sensates, anti-caking agents, antifoaming agents, antimicrobial agents, binders, biological additives, buffering agents, bulking agents, chemical additives, denaturants, polymer beads, film formers or materials, opacifying agents, pH adjusters, propellants, reducing agents, and sequestrants. In that the formulations of the present invention are to treat an actinic induced lesion, the formulations may suitably contain a sun screen.

In regard to verapamil formulations, this calcium channel blocker is a derivative of papaverine, which will deteriorate rapidly in the presence of heavy metals. Thus, verapamil formulations may be affected by the presence of heavy metal ions that originate from the mixing containers or equipment. Thus a chelating agent may suitably be included in the formulation. Suitable chelating agents may be any of those known to those skilled in the art, such as the ones selected from the group comprising phosphonate chelating agents, amino carboxylate chelating agents or other carboxylate chelating agents, or polyfunctionally-substituted aromatic chelating agents or mixtures thereof. Suitable amino carboxylate chelating agents useful herein include ethylenediaminetetraacetates, e.g., edetate disodium.

Antioxidants may suitably be added to prevent oxidation of components of the formulations. For example, it was found that the ethoxdiglycol reagent of the exemplified formulations was reacting with air and forming byproducts including, but not limited to, aldehydes, peroxides and free radicals, which cause drug crystallization and subsequent loss of therapeutic potency. These by-products may also cause skin irritation. Non-limiting examples of antioxidants that can be used with the compositions of the present invention include acetyl cysteine, ascorbic acid, ascorbic acid polypeptide, ascorbyl dipalmitate, ascorbyl methylsilanol pectinate, ascorbyl palmitate, ascorbyl stearate, BHA, BHT, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

Air has the potential to be entrained into the materials during the stages of formulation. Thus, in some embodiments nitrogen, $N_2$, is used to purge all containers during chemical addition and mixing. Additionally, during mixing, a vacuum may be employed to reduce the addition of entrained air. In some embodiments, ointment tubes are purged just prior to filling and sealing. In these embodiments, the nitrogen serves as a replacement for entrained air and is non-reactive with the components.

In some embodiments, a "non-reactive" glaminate ointment tube is used so that no reaction occurs with the ointment tube.

In some embodiments, a penetration enhancer may suitably be added to the formulation, thereby increasing the amount of the calcium channel blocker in the target tissue. Non-limiting examples of penetration enhancers which may be used in the compositions herein include, for example, 2-methyl propan-2-ol, propan-2-ol, ethyl-2-hydroxypropanoate, hexan-2,5-diol, POE(2) ethyl ether, di(2-hydroxypropyl) ether, pentan-2,4-diol, acetone, POE(2) methyl ether, 2-hydroxypropionic acid, 2-hydroxyoctanoic acid, propan-1-ol, 1,4-dioxane, tetrahydrofuran, butan-1,4-diol, propylene glycol, polyoxypropylene 15 stearyl ether, octyl alcohol, POE ester of oleyl alcohol, oleyl alcohol, lauryl alcohol, dioctyl adipate, dicapryl adipate, di-isopropyl adipate, di-isopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, iso-propyl palmitate, ethyl laurate, 2-ethylhexyl pelargonate, iso-propyl isostearate, butyl laurate, benzyl benzoate, butyl benzoate, hexyl laurate, ethyl caprate, ethyl caprylate, butyl stearate, benzyl salicylate, 2-hydroxypropanoic acid, 2-hyroxyoctanoic acid, dimethyl sulphoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, and, 1-dodecylazacyloheptan-2-one.

Thus, for example, the concentration of calcium channel blocker is a formulation suitable for topical administration to a subject may be about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, or greater amount by weight, or any amount by weight or range by weight derivable therein. In particular embodiments, the formulation includes about 1% to about 30% by weight of calcium channel blocker. In certain particular embodiments, the calcium channel blocker is verapamil, and the formulation of verapamil for topical delivery is 15% verapamil by weight. For example, the verapamil may be Verapamil 15 Topical Gel (VTG 15%), compounded by Prescription Dispensing Laboratories, San Antonio, Tex.

As discussed above, the formula may include additional components, which by way of example include agents that facilitates spreading or application of the composition on a surface, semi-solid and gel-like vehicles, thickening agents, water, preservatives, emulsifiers, antioxidants, sunscreens, solvents, absorbents, fragrances, essential oils, skin sensates, anti-caking agents, antifoaming agents, antimicrobial agents, binders, biological additives, buffering agents, bulking agents, chemical additives, denaturants, polymer beads, film formers or materials. The additional components may represent be about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 65%, about 70%, about 75%, about 80%, about 85%, about 90%, about 95%, or greater amount by weight, or any amount by weight or range by weight derivable therein. For example, in some embodiments, the formulation includes about 5% to about 20% by weight of verapamil HCL, about 10% to about 20% by weight of ethoxydiglycol, about 0.2% to about 1.0% by weight of propylene glycol, about 10% to about 15% by weight of lecithin soya granular, about 10% to about 15% by weight of isopropyl myristate, about 0.01% to about 0.15% by weight of sorbic acid, about 0.01% to about 0.5% by weight of BHT, about 5% to about 15% by weight of pluronic F127, about 0.001% to about 0.2% by weight of potassium sorbate, about 20% to about 50% by weight of water, about 0.001 to about 0.05% by weight of disodium edetate.

Variants of the above formula can be made. Examples of such variants include, but are not limited to: inclusions of preservatives such as, either individually or as mixtures, methylparaben NF, propylparaben NF, and Germall, omission of a chelating agent, e.g., disodium edetate; omission of other ingredients, such as sorbic acid and/or potassium sorbate.

Suitable formulations are also disclosed in U.S. Pat. Nos. 6,031,005, 6,353,028 and 6,525,100 and U.S. Application Publication Nos. 20040171684 and 20040170675, all incorporated herein by reference.

III. Administration Regimens

The calcium channel blocker can be administered in accordance with any regimen known to those of ordinary skill in the art. For example, administration can be topical, intravenous, intralesional, and so forth. One of ordinary skill in the art would be familiar with the various methods by which pharmacological agents can be administered to a subject. In certain particular embodiments of the present invention, administration is topical. Formulations for administration of calcium channel blockers are discussed above.

An effective amount of calcium channel blocker is determined based on the intended goal, for example (i) decrease in size of one or more AK lesions, (ii) decreased inflammation of AK lesions, or (iii) prevention of AK.

The dose of calcium channel blocker to be administered, both according to number of treatments and dose, may depend on various factors, including the size of AK, location of AK, and the extent of inflammation of AK. Precise amounts of the therapeutic composition also depend on the judgment of the practitioner and are peculiar to each individual.

In embodiments wherein the calcium channel blocker is administered topically, the topical formulation may be applied to the surface of the AK, which may or may not include an area of skin surrounding the AK. For example, the area to be treated may be an area encompassing the AK that measures about 2"×2", 3"×3", or any area of any size, so long as the AK is topically treated. The preparation comprising the calcium channel blocker may be thoroughly rubbed into the surface of the AK by the subject.

In some embodiments, the calcium channel blocker formulated for topical delivery may require administration using an applicator, such as a sponge or pad. In other embodiments, the calcium channel blocker is administered in the form of a patch or strip, such as a transdermal delivery device. The transdermal delivery device may be any transdermal delivery device known to those of ordinary skill in the art. A "transdermal delivery device" is defined herein to refer to a patch comprising a therapeutic agent that can be applied to the surface of the skin for the purpose of transdermally delivering a therapeutic agent. For example, the transdermal delivery device can include a patch (or backing layer), a reservoir to include the verapamil and any additional agent discussed above, and optionally an adhesive layer.

The frequency of administration can be any frequency that is suspected or known to be of benefit in the treatment or prevention of AK. For example, the frequency of administration may be once a day, twice a day, three times a day, four times a day, every other day, every third day, every forth day, once a week, once a month, or any greater or lesser frequency of administration to achieve the desired effect. In certain particular embodiments, the frequency of administration is twice a day.

The frequency of administration may increase or decrease during the course of therapy, as determined by a practitioner, based on the response of AK to therapy. For example, if a response is observed after 1 week of therapy, the frequency of application may be decreased. Alternatively, if a response is not observed within a predetermined period of time, the frequency of administration may be increased. Alternatively, the concentration of calcium channel blocker in the formulation may be adjusted, rather than the frequency of administration. One of ordinary skill in the art would be familiar with therapeutic regimens, and modification of a therapeutic regimen in response to therapy.

The duration of therapy can continue for any period of time, as determined by a practitioner. Factors to be included in assessing duration of therapy include response of the AK to therapy, patient characteristics, and so forth. For example, treatment duration may be about 1 day, about 2 days, about 3 days, about 4 days, about 5 days, about 6 days, about 1 week, about 10 days, about 2 weeks, about 3 weeks, about 4 weeks, about 5 weeks, about 6 weeks, or any greater or lesser duration, or any duration derivable therein.

When the calcium channel blocker is formulated for topical administration, the formulation may be a gel, cream, ointment, dispersion, oil, coating, solution, or any formulation for topical administration known to those of ordinary skill in the art. Formulations are discussed in greater detail elsewhere in this specification. The amount of calcium channel blocker in the topical formulation can be any amount known or suspected to be of benefit in the treatment or prevention of AK. For example, the amount to be applied topically may be about 0.1 ml, about 0.15 ml, about 0.2 ml, about 0.25 ml, about 0.30 ml, about 0.35 ml, about 0.4 ml, about 0.45 ml, about 0.50 ml, about 0.55 ml, about 0.60 ml, about 0.65 ml, about 0.70 ml, about 0.75 ml, about 0.80 ml, about 0.85 ml, about 0.9 ml, about 0.95 ml, about 1.0 ml, about 1.1 ml, about 1.2 ml, about 1.3 ml, about 1.4 ml, about 1.5 ml, about 1.6 ml, about 1.7 ml, about 1.8 ml, about 1.9 ml, about 2.0 ml, about 2.2 ml, about 2.5 ml, about 3.0 ml, about 3.5 ml, about 4.0 ml, about 4.5 ml, about 5.0 ml, or more, or any amount derivable therein.

The subject to be treated can be any subject that can be afflicted by AK. For example, the subject can be either male or female. The subject can be of any age. The AK can be located on any part of the body. In certain particular embodiments, the subject is a man or woman age 18 and older which a clinical diagnosis of four to eight AK lesions within a contiguous 25 $cm^2$ treatment area on the face, hands, or balding scalp.

Patients should be screened to confirm if they are being treated with digitalis, a digitalis derivative, and/or cyclosporine. If so, the blood levels of these drugs should be monitored since verapamil may decrease the clearance rate of these drugs, thereby resulting in possible toxicity of these agents.

Subjects can be evaluated at any interval by a qualified practitioner to assess response to therapy. For example, patients may be evaluated monthly by a qualified physician. Lesions will be evaluated for measurement of a response. A response can include any measure of response known to those of ordinary skill in the art. For example, a response can be measured by determining absolute and/or percent reduction in lesion number, absolute and/or percent reduction in lesion area, absolute and/or percent reduction in lesion volume, reduction in lesion irritation (as measured by stinging and burning; rating scale), erythema (rating scale), and absolute and/or percent reduction in brown spots. Patients will also be evaluated for any evidence of local or systemic toxicity.

IV. Combination Therapies

The methods of the present invention may be combined with a wide variety of surgical and non-surgical therapies for actinic keratoses (AK). The combination of treatment methods selected will depend on variables including medical status of the patient; lesion characteristics such as size, location, duration, and change in growth pattern; previous treatment; and certain anatomic locations such as the scalp and ear.

Cryosurgery deals with the therapeutic application of cold at profoundly low temperatures (those below 0° C.) for the purpose of destroying tissues in selected target sites. The freezing process induces coagulation necrosis and is confined to the tissues within the region of the application and the ice ball. The American Academy of Dermatology Committee on Guidelines of Care has published Guidelines of Care for Cryosurgery, (Guidelines, 1994) The degree and extent of tissue destruction depend largely on the size of the ice ball and the temperatures within it. In regard to cryosurgery, freezing temperatures of a cryogenic agent applied directly or indirectly to the skin causes local destruction of tissue. Multiple or repeated treatments may be applied as indicated. Cryogens useful for cryosurgery include liquid nitrogen, which is the most often used cryogen for cryosurgery treatment of AK; other cryogens include, for example, solidified carbon dioxide; nitrous oxide; freons; and helium. The cryogens can be applied by a variety of known means including cotton-tipped applicator, open-spray, open-cone (confined spray), closed-cone, cryoprobe, and metal applicator. Freeze time varies according to the cryogen used and the size of the AK lesion, but generally ranges from 3 to 60 seconds.

Other surgical therapy useful for treatment of AK includes shave removal or excision with a scalpel, optionally followed by electrocautery to stop bleeding; dermabrasion, which can involve sanding off the top layers of the lesion with a rapidly rotating brush; laser surgery with, for example a carbon dioxide laser, to remove the skin to the desired depth; and electrosurgical skin resurfacing, using radiofrequency energy to remove skin layers without heat. In lesions suspected of being invasive squamous cell carcinomas, excision has an advantage of providing a diagnosis as well as treating the lesion.

5-FU may be applied as is known in the art. For example, one commercially available product, Efudex® (imiquimod), a 2% or 5% topical solution or a 5% topical cream of 5-fluorouracil supplied by Roche Laboratories Inc., is recommended to be applied twice daily in an amount sufficient to cover the lesions. The usual duration of therapy with Efudex® is estimated by Roche to be from two to four weeks. Another fluorouracil containing product that is commercially available is Fluoroplext, a 1% topical cream or solution sold by Allergan, Inc. Fluoroplex(® is recommended to be applied twice daily over a period of two to six weeks. Carac® is a microsphere-encapsulated 0.5% fluorouracil cream commercially available from Dermik Laboratories, and is to be applied twice daily for 2 to 4 weeks.

Diclofenac, a nonsteroidal anti-inflammatory agent, is used as a 3% gel in the treatment of AK. The gel is applied twice daily for 2-3 months with results often not being evident with single usage for up to a month after completion of the therapy. Diclofenac gel is available as Solraze™, distributed by Bioglan Pharma.

Imiquimod is an immune response modifier, that is approved by the FDA for the treatment of AK. Imiquimod stimulates the local immune system by inducing interferon-α, -β, and -γ and TNF-α. It is commercially available as Aldara™, a 5% cream from 3M, and is used twice weekly for 16 weeks.

One or more photosensitizing agents can be used to treat AK in combination with the method of the present invention. Photosensitizing agents are photoactivatable compounds and complexes that, upon irradiation, cause damage to cells. The photochemical reaction resulting from activating a photosensitizing agent is believed to generate chemical disruptive species, such as oxygen radicals, that interacts with cellular constituents leading to cell death.

Suitable photosensitizing agents include 5-aminolevulinic acid (5-ALA). 5-ALA is metabolically converted to the photosensitizing agent, protoporphyrin IX, after administration to a subject. 5-ALA is available under the brand name Levulan.RTM. as a topical solution, 20%, containing the hydrochloride salt of 5-ALA. 5-ALA is metabolically converted after uptake by cells to protoporphyrin IX, which can be photoactivated by blue light at 6-10.9 J/cm.sup.2. Photoactivation typically occurs 14 to 18 hours after application of 5-ALA, while blue light treatment lasts about 17 minutes.

Other pharmacological therapies useful for treatment of AK can be used with the invention. For example, therapies useful for the treatment of AK may suitably include retinoids (vitamin A derivatives), a-hydroxy acids and intralesional interferon injections. Any effective route of administration can be used, e.g., retinoids can be administered topically or systemically. Topical retinoids are typically in the form of creams and include Retin A®. and Avita®. Caustic agents, such as trichloroacetic acid, phenol, or other known caustic agents can be used as adjuvant therapies to the AK treatments of the present invention. Treatment with caustic agents cause the top layer of skin to slough off and trigger new skin growth.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Examples of two formulations suitable for the delivery of verapamil according to the present invention are shown in Table 1.

TABLE 1

| Phase | Ingredients | 10% Verapamil Formulation % by weight | 15% Verapamil Formulation % by weight |
|---|---|---|---|
| A | Verapamil HCl | 10.00 | 15.00 |
| A | Ethoxydiglycol | 14.00 | 19.50 |
| A | Propylene Glycol | 0.50 | 0.50 |
| B | Lecithin Soya Granular | 13.10 | 13.10 |
| B | Isopropyl Myristate | 13.10 | 13.10 |
| B | Sorbic Acid | 0.09 | 0.09 |
| C | Butylated Hydroxy Toluene (BHT) | 0.10 | 0.10 |
| D | Pluronic F127 | 9.80 | 11.60 |

TABLE 1-continued

| Phase | Ingredients | 10% Verapamil Formulation % by weight | 15% Verapamil Formulation % by weight |
|---|---|---|---|
| D | Potassium Sorbate | 0.15 | .012 |
| D | Purified Water | 39.15 | 26.88 |
| E | Disodium Edetate | 0.01 | 0.01 |

To make phase A, dissolve verapamil in other ingredients of this phase with the aid of heat (90-100° C.), and stir during this dissolving step. When the solution is clear, weigh to ascertain the amount of evaporation and add the amount lost to evaporation back as ethoxydiglycol. Immediately add phase B and C and stir well. To make phase B, disperse lecithin and sorbic acid in isopropyl myristate, allow to stand at room temperature until a liquid of syrup consistency forms. Stir well and store in a light protected container. To make phase D, combine ingredients, using refrigerated water. Make sure that all the granules are wet, and place in a refrigerator. Mixture will form a clear solution over 24-48 hours. Alternatively, the mixture can be uniformly mixed with a mixing blade. It will take on the appearance of beaten egg whites. When placed in the refrigerator it will form a clear solution much faster, usually overnight. To D add E, and stir gently to dissolve D while avoiding foaming. Gently add phase A to phase C, avoiding the incorporation of air by purging with nitrogen. Stir for 10 minutes using a 3 inch mixing blade at 3100 rpm. Dispense in 30 gm glaminate ointment tubes.

Additionally, all ingredients may be mixed together under controlled temperature, under vacuum conditions, and by utilizing countermotion stirring and shear with various size mixing blades at varying rpms.

Example 2

Pilot Study Demonstrating Effectiveness of Topical Verapamil in the Treatment for Actinic Keratosis Patient 1. Subject treated AK on both sides of receding hairline and forehead with a 15% verapamil topical gel prepared by Prescription Dispensing Laboratories, San Antonio, Tex. Approximately 0.5 ml was applied nightly for about 2 months, the dose being rubbed into the skin for about 5 minutes. During the treatment some peeling and redness on the lesions was noted that lasted until the AK lesions were gone, although the subject reported neither itching nor pain. Upon resolution of the AK lesions, the skin was noticeably smoother and even and appeared to have a "shine" to it.

After the treatment had been discontinued for a couple of months, additional lesions began to appear, although the subject stated they had a reduced severity as compared to previous lesions.

Patient 2. Verapamil 15 Topical Gel (VTG 15%), was obtained from Prescription Dispensing Laboratories, San Antonio, Tex. An additional male patient with a diagnosis of AK was identified for participation in the pilot study to evaluate the efficacy of topical verapamil in the treatment of AK. The patient was diagnosed with an AK on the head and hand. VTG 15% topical gel was applied to the surface of the AK lesions twice a day, and thoroughly rubbed in. After two to three weeks of treatment, clinically significant reduction in the lesions was noted, with minimal irritation or inflammation of the lesions. Both lesions decreased about 80% in size after a few weeks treatment.

Patient 3. A 68-year-old female patient had recurring AK on her face, neck, and arms. The patient had used Efudex (5% fluorouracil) multiple times over a period of a year. The patient reported significant pain, itching and discomfort with use of the product. It did not appear to "cure" the AK. The patient had also used Cerac (0.5% fluorouracil) and did not have reactions as severe as with the use of the Efudex. However, the results were not as good, and most lesions came back. Periodically, the patient would have to supplement the topical treatment of her AK with doctor office visits where freezing, scraping, and surgical removal of the lesions were required.

1. The patient began using verapamil 15% topical gel (VTG 15%) on a single AK lesion, which had the appearance of a "scab," that remained after a year from treatment with Cerac. The lesion would itch and not go away. After treatment with VTG 15%, the lesion is no longer detectable.

2. The patient had a single AK lesion, which had the appearance of a "scab," above the thumb on her right hand. After applying VTG 15% over the entire upper right hand, two new lesions "appeared." All formed slightly rough textures which have currently sloughed off and have not returned.

3. The patient's upper left hand had been cured of AK lesions ("scabby keratosis") over the years by freezing and treatments with Efudex and Carac, but only the freezed ones did not return. She used the VTG 15% topical gel on the entire upper left hand for 4 weeks, and the area has smoothed out.

4. After treating her lower right arm with VTG 15% for 4 weeks, where only one actual lesion had persisted for some time, two additional lesions appeared. After 4 weeks of treatment, they are still visible but appear to be healing.

5. The patient had an AK lesion (which had the appearance of a "scab") on her upper left forehead which was treated with VTG 15% with no apparent improvement.

6. The patient began treating her now (½ inch square on the bridge of her nose) that had been recommended for surgery. The skin was rough, peeled easily and would bleed and hurt when cleaned (such as following make-up removal). After treatment with VTG 15% for 6 weeks, the area has softened, the bleeding is less frequent (rare), and no more pain is experienced.

Example 3

Open-Label, Non-Blinded, One Subject Trial of the Use of Topical Verapamil in the Treatment of Actinic Keratosis The patient was a male who, on examination, was found to have 15 to 4 lesions that appeared as thin, pink, slightly crusted plaques scattered across the forehead and anterior scalp. The patient was clinically diagnosed with AK. Following informed consent for a biopsy and for participation in this clinical trial, a biopsy specimen was obtained from his right forehead. The pathology diagnosis was "solar keratosis, early." In particular, the biopsy specimen showed atypical keratinocytes in the lower portion of the epidermis and a few very small buds of atypical keratinocytes emanating from the undersurface of the epidermis. Some of their nuclei appeared large, hyperchromatic, and pleomorphic, and a few kyskeratotic cells were seen.

The subject topically applied 15% verapamil gel to the lesions twice daily over a period of seven weeks. The patient felt that the lesions receded and/or cleared with no significant side effects. The number of AK was reduced following the seven week course of therapy. Based on its apparent, short-term safety profile, and the results set forth in these Examples, additional clinical trials to further establish the clinical efficacy and safety of topical verapamil are warranted.

Example 4

Clinical Trial of the Use of Topical Verapamil in the Treatment of Aktinic Keratosis Rationale. Verapamil, a calcium channel blocker, may act to block the entry of divalent calcium into cells, resulting in the maturation of fibroblast collagenase and subsequent degradation or remodeling of the fibrotic tissue. Verapamil has been reported in the literature to exhibit anti-tumor activity and to enhance the effectiveness of chemotherapy. In view of the above pilot results, a clinical trial can be conducted to evaluate the efficacy of verapamil in the treatment of AK.

Formulation. The preferred formulation of Verapamil for evaluation in the clinical trial will be Verapamil 15 Topical Gel (VTG 15%), compounded by Prescription Dispensing Laboratories, San Antonio, Tex. Other formulations can be evaluated as well. For example, Verapamil may or may not be incorporated into a transdermal vehicle. Verapamil can be formulated not only as a gel, but as a cream, lotion, oil, dispersion, coating, or other formulation known to those of ordinary skill in the art for topical application. It can also be formulated for application via a transdermal delivery device, such as a patch, tape, or a solution. The verapamil can be formulated to include one or more additional agents known or suspected to be of benefit in the treatment of AK.

Study Participants. Healthy men and women age 18 and older which a clinical diagnosis of four to eight AK lesions within a contiguous 25 cm$^2$ treatment area on the face, hands, or balding scalp.

Exclusion Criteria. Patients should be screened to confirm if they are being treated with digitalis, a digitalis derivative, and/or cyclosporine. If so, the blood levels of these drugs should be monitored since verapamil may decrease the clearance rate of these drugs, thereby resulting in possible toxicity of these agents. Females of child bearing age will not be included in the study due to the reported possible teratogenicity of verapamil.

Dose. 0.5 ml of topical verapamil will be applied to each 2"×2" affected area twice a day. The topical verapamil will be rubbed in thoroughly. As set forth above, the preferred formulation for evaluation will be Verapamil 15 Topical Gel (VTG 15%), compounded by Prescription Dispensing Laboratories, San Antonio, Tex.

Duration of Treatment. Eight to twelve weeks.

Evaluation. Patients will be evaluated monthly by a qualified physician. Lesions will be evaluated for lesion number (absolute and percent reduction), lesion area (absolute and percent reduction), lesion volume (absolute and percent reduction), irritation (stinging and burning; rating scale), erythema (rating scale), and reduction in brown spots (absolute and percent reduction). Patients will also be evaluated for any evidence of local or systemic toxicity.

REFERENCES

The following references, to the extent that they provide exemplary procedural or other details supplementary to those set forth herein, are specifically incorporated herein by reference.

U.S. Pat. No. 6,031,005
U.S. Pat. No. 6,353,028
U.S. Pat. No. 6,525,100
U.S. Patent Pub. 20040171684
U.S. Patent Pub. 20040170675
Ackerman, *J. Am. Acad. Dermatol.,* 45:467-469, 2001.
Fitscha et al., *Leukot. Essent. Fatty Acids,* 45:289-291, 1992.
Frost and Green, *Br. J. Dermatol.,* 455-464, 1994.
Heaphy and Ackerman, *J. Am. Acad. Dermatol.,* 43:138-150, 2000.
Guidelines, *J. Am. Acad. Dermatol.,* 31:648-653, 1994.
Jeffes and Tang, *Am. J. Clin. Dermatol.,* 1:167-179, 2000.
Jorizzo et al., *Cutis,* 6(Suppl.):9-7, 2004.
Lober and Fenske, *Am. J. Clin. Dermatol.,* 5:395-401, 2004.
Memnon et al., *Brit. J. Dermatol.,* 144:437-438, 2001.
Rodler et al., *J. Mol. Cell Cardiol.,* 27:2295-2302, 1995.
Roth et al., *Proc. Natl. Acad Sci. USA,* 93: 5478-5482, 1996.
Salasche, *J. Am. Acad. Dermatol.,* 42:4-7, 2000.
Stetler-Stevenson et al., *Amer. J. Pathol.,* 148:1345-1350, 1996.
Topical Diclofenac, *Prescrire Int.,* 13:138-139, 2004.

What is claimed is:

1. A method for the treatment of actinic keratosis on an area of skin of a subject in need of such treatment, comprising contacting said skin with an effective amount of a calcium channel blocker.

2. The method of claim 1, wherein said skin is contacted topically with a diphenylalkylamine calcium channel blocker, a dihydropyridine calcium channel blocker, or a benzothiazepine calcium channel blocker.

3. The method of claim 2, wherein the diphenylalkylamine calcium channel blocker is verapamil.

4. The method of claim 2, wherein the dihydropyridine calcium channel blocker is amlodipine, barnidipine, benidipine cilnidipine efonidipine felodipine, isradipine, nacidipine nercanidipine manidipine, nicardipine, nifedipine, nilvadipine, nimodipine, nisoldipine, or nitrendipine.

5. The method of claim 2, wherein the benzothiazepine calcium channel blocker is diltiazem.

6. The method of claim 1, wherein said skin is contacted topically with a formulation comprising verapamil.

7. The method of claim 6, wherein said verapamil is present in said formulation in the range of about 10% to about 15% by weight.

8. The method of claim 7, wherein said formulation comprises isopropyl myristate and lecithin soya granular in approximately equal amounts by weight.

9. The method of claim 8, wherein the combined amount of isopropyl myristate and lecithin soya granular is in the range of about 25% to about 30% by weight.

10. The method of claim 9, wherein said formulation comprises pluronic F127.

11. The method of claim 10, wherein said formulation further comprises pluronic F127 in the range of about 8% to about 14% by weight.

12. The method of claim 9, wherein said formulation further comprises ethoxyglycol.

13. The method of claim 12, wherein said formulation comprises ethoxyglycol in the range of about 14 to about 20% by weight.

14. The method of claim 12, wherein said formulation further comprises BHT.

15. The method of claim 14, wherein said formulation further comprises about 0.1% by weight BHT.

* * * * *